United States Patent [19]

Kim et al.

[11] Patent Number: 5,786,460
[45] Date of Patent: Jul. 28, 1998

[54] ANTIFUNGAL ANTIBIOTIC CEPACIDINE A

[75] Inventors: Sung Ho Kim, Seoul; Bong Chul Hyun, Ichun-kun; Jung Woo Suh; Chang One Kim, both of Seoul; Yoong Ho Lim, Suwon; Chul Hoon Lee, Seoul, all of Rep. of Korea

[73] Assignee: Cheil Foods & Chemicals, Inc., Seoul, Rep. of Korea

[21] Appl. No.: 632,458

[22] PCT Filed: Oct. 17, 1994

[86] PCT No.: PCT/KR94/00139

§ 371 Date: Jun. 18, 1996

§ 102(e) Date: Jun. 18, 1996

[87] PCT Pub. No.: WO95/11310

PCT Pub. Date: Apr. 27, 1995

[30] Foreign Application Priority Data

Oct. 22, 1993 [KR] Rep. of Korea .................. 93-22089

Oct. 22, 1993 [KR] Rep. of Korea .................. 93-22090

[51] Int. Cl.$^6$ .................. C07H 17/08; C12P 19/60; C12N 1/00

[52] U.S. Cl. .................. 536/6.5; 435/75; 435/77; 435/822

[58] Field of Search .................. 536/6.5; 435/75, 435/77, 822

[56] References Cited

U.S. PATENT DOCUMENTS 5,189,150  2/1993  Zeeck et al. .................. 536/6.5

*Primary Examiner*—Elli Peselev
*Attorney, Agent, or Firm*—Burns, Doane, Swecker & Mathis, L.L.P.

[57] ABSTRACT

Novel antifungal antibiotics Cepacidine A ($A_1$ and $A_2$), a novel microorganism *Pseudomonas cepacia* AF 2001 producing the same, and a process for producing the said antibiotics are disclosed.

3 Claims, 6 Drawing Sheets

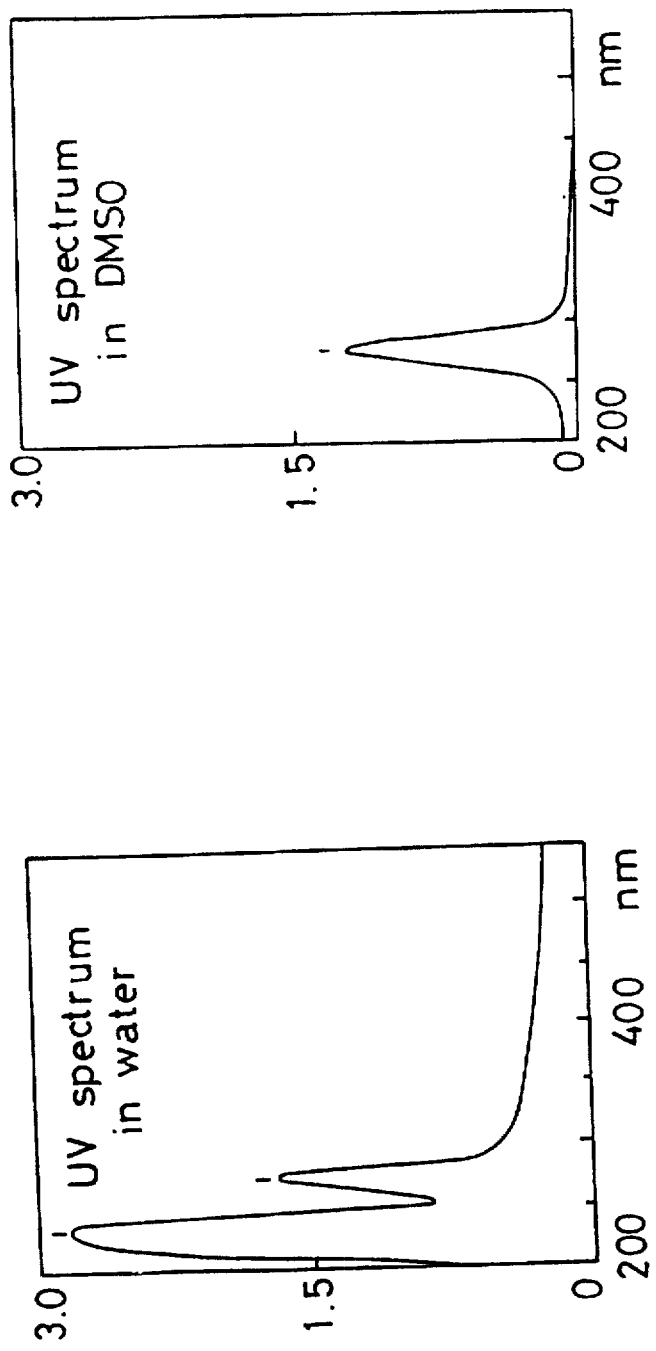
Fig. 1 UV Spectrum of Cepacidine A

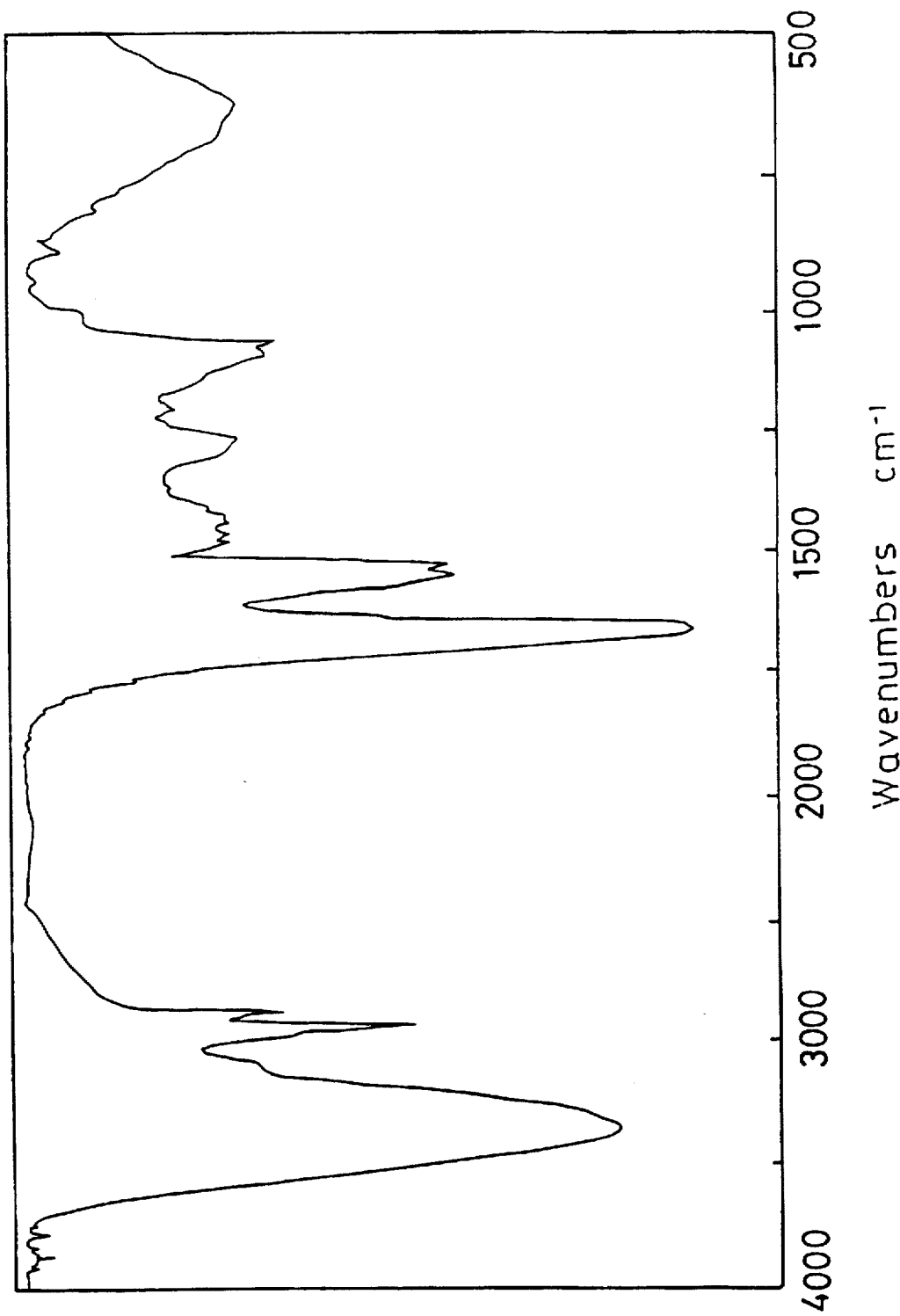

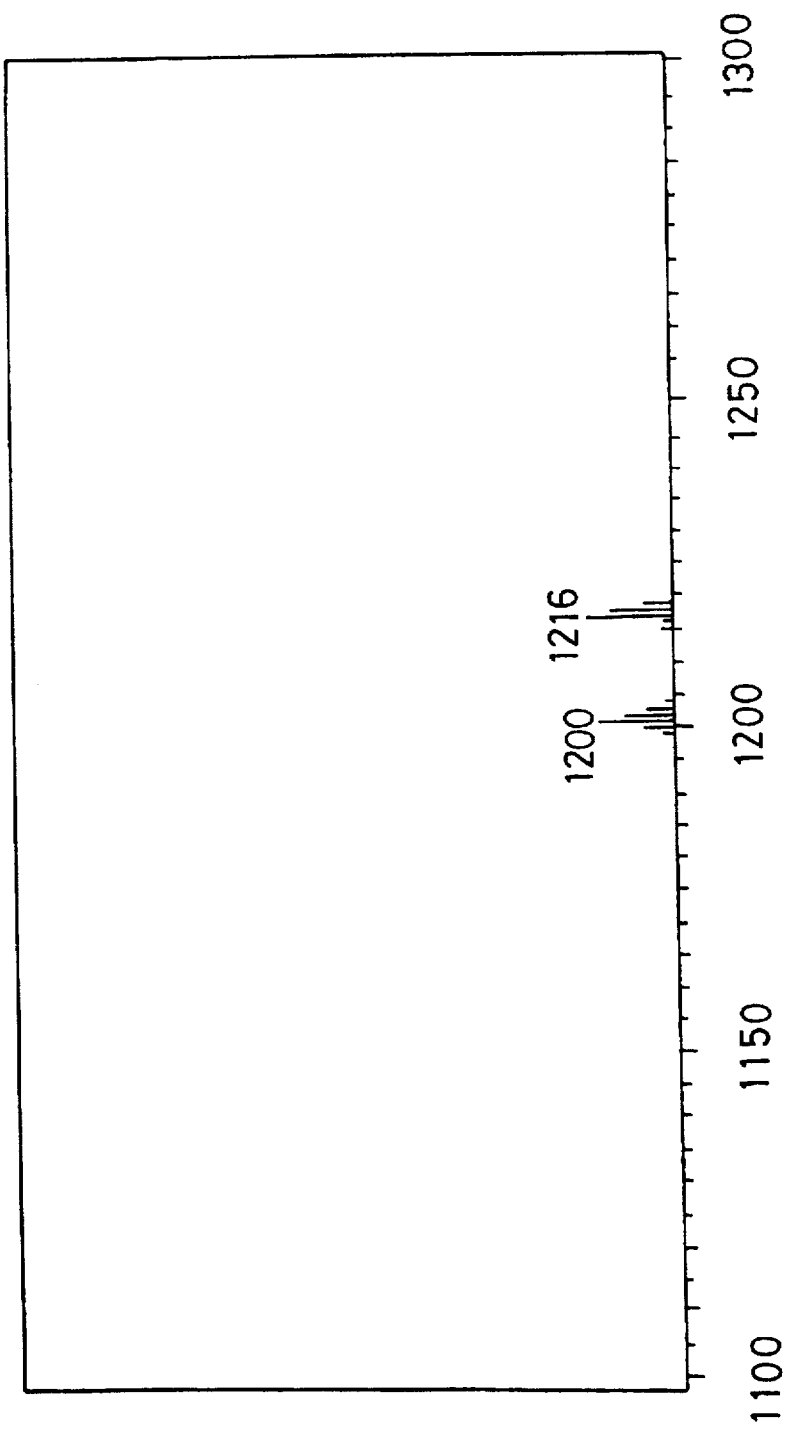
Fig. 3 FAB/MS Spectrum of Cepacidine A

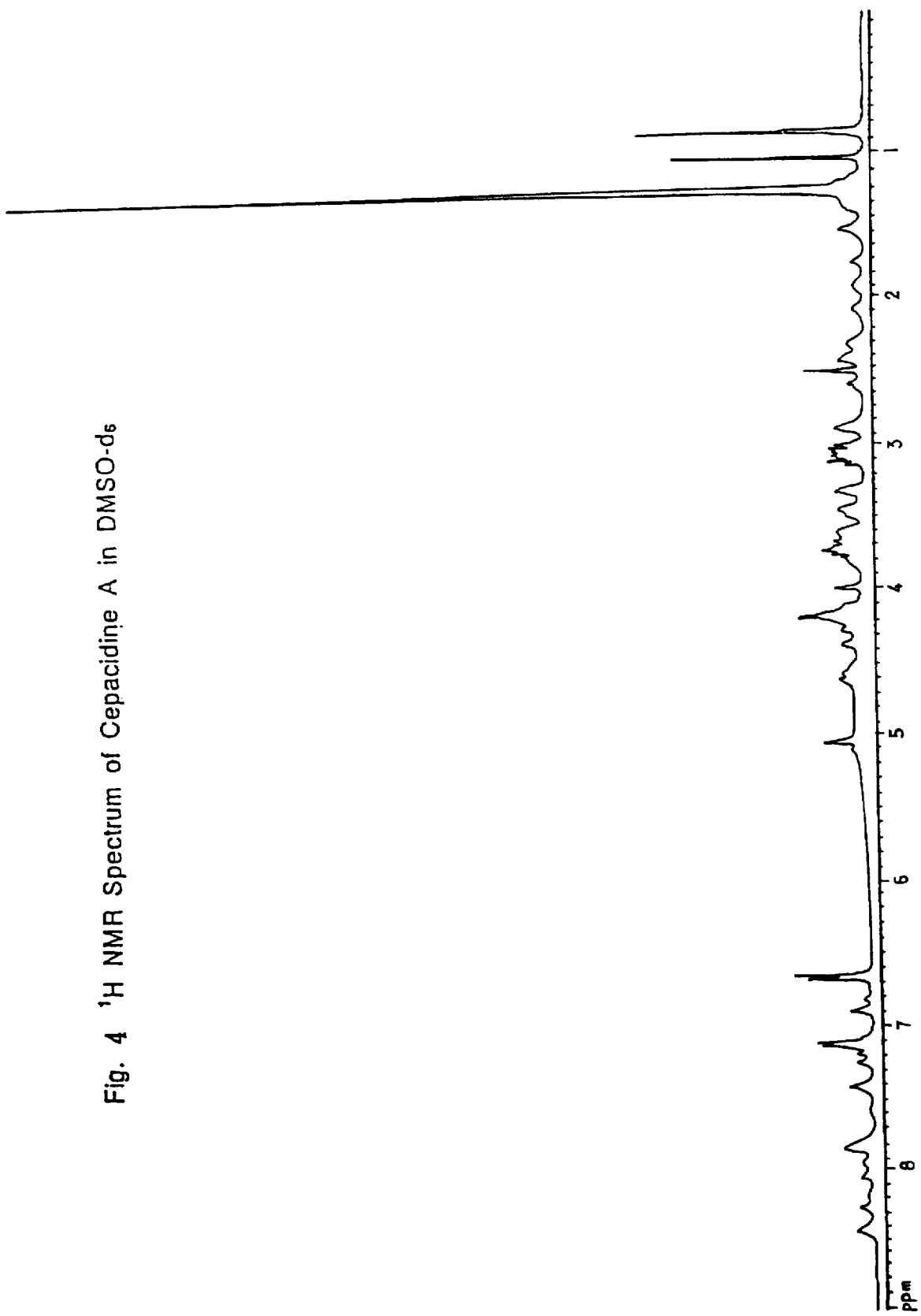

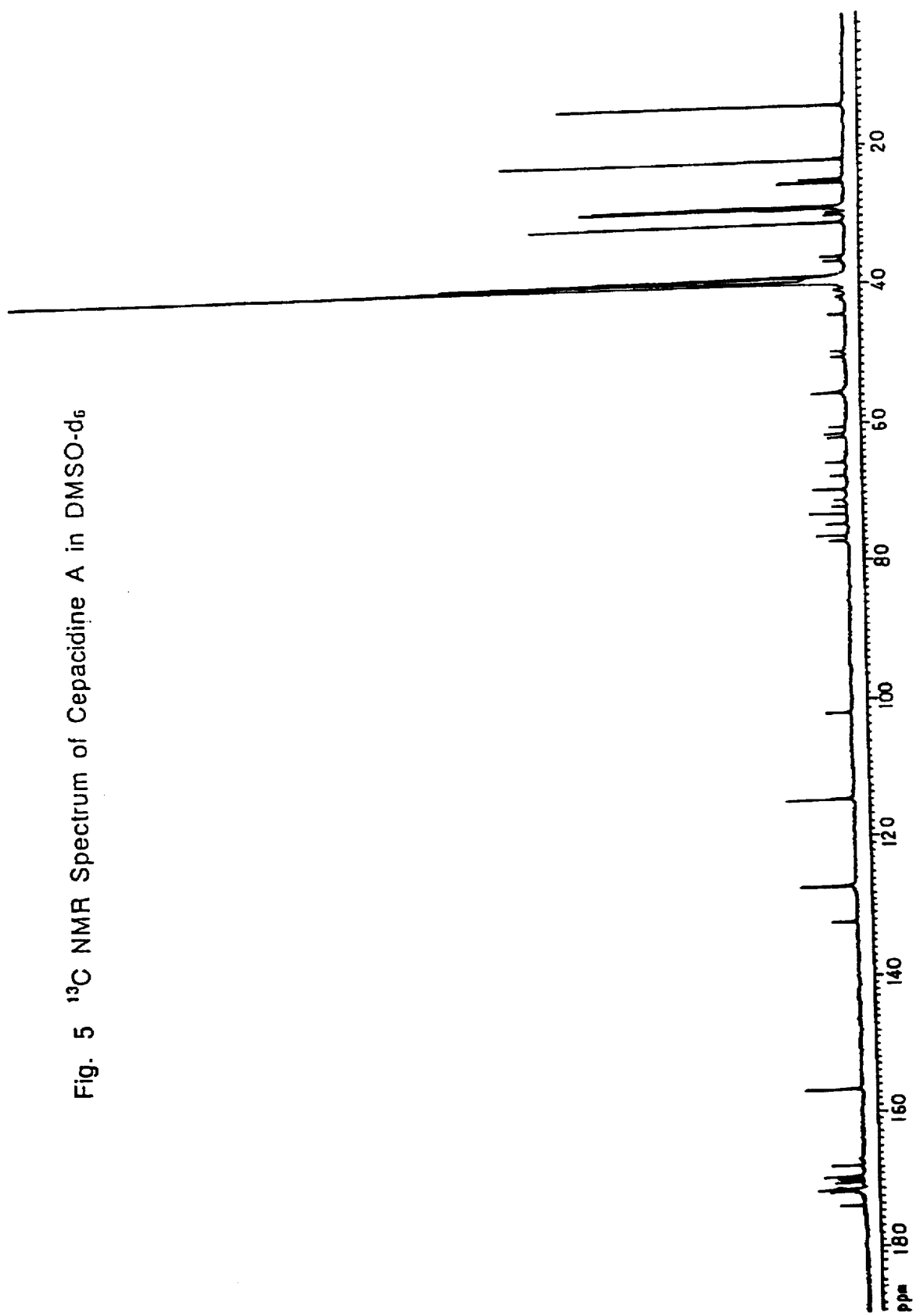
Fig. 5 $^{13}$C NMR Spectrum of Cepacidine A in DMSO-$d_6$

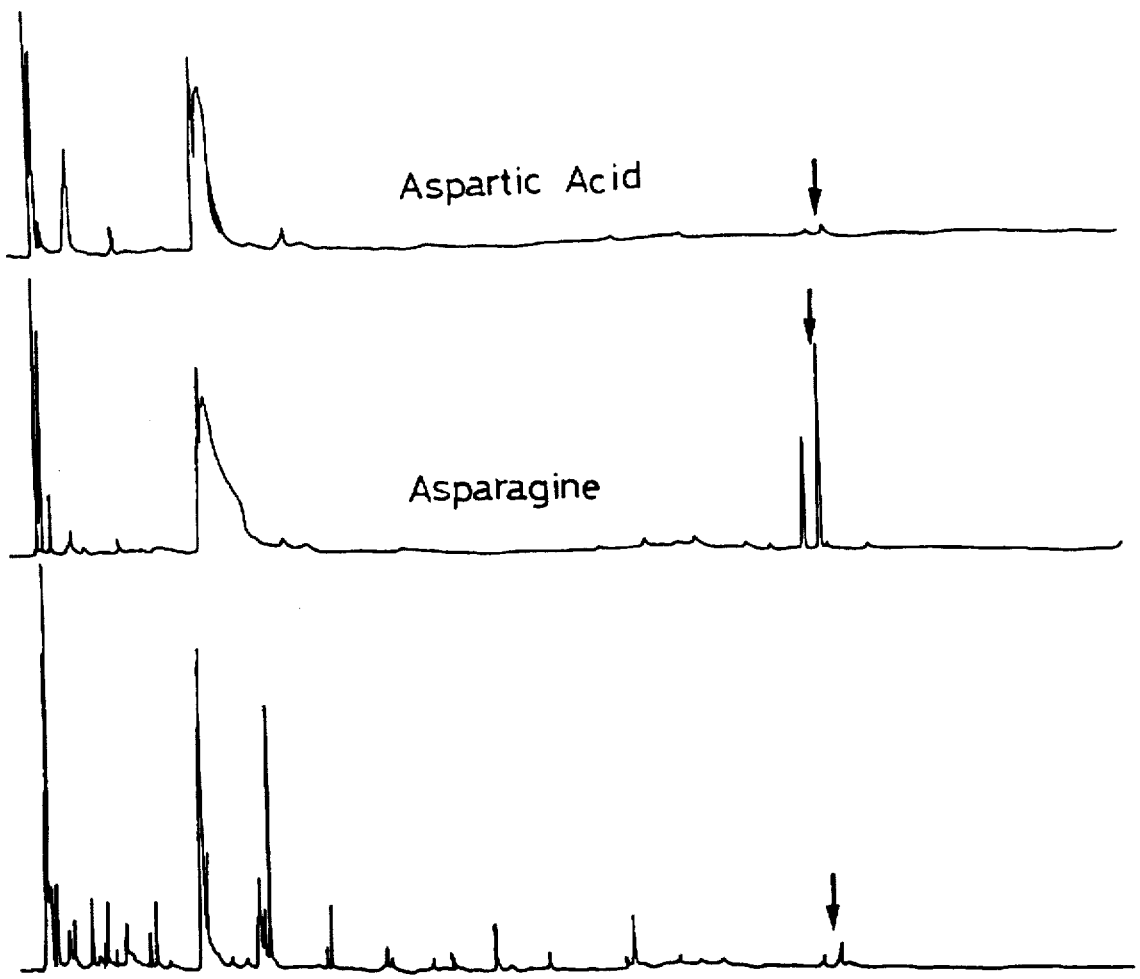
Fig. 6 The Pyrolyzed Gas Chromatograms of Asp(top), Asn(middle) and Cepacidine A(bottom)

ANTIFUNGAL ANTIBIOTIC CEPACIDINE A

BACKGROUND OF THE INVENTION

1. Field of the Invention

The present invention relates to novel antifungal antibiotics Cepacidine A($A_1$ and $A_2$), a novel microorganism *Pseudomonas cepacia* AF 2001 producing the same, and a process for producing the said antibiotics.

2. Description of the Prior Art

As a variety of antifungal agents such as griseofulvin, nystatin, amphotericin-B and the like were separated from actinomycetes, chemotherapies for the treatment of fungal infections have been established. Another group of antifungal agents such as blasticidin, kasugamycin, polyoxin and validamycin was separated from actinomycetes and has been utilized in controlling fungal infections of plants. Thereafter, many antifungal substances were not only separated from various microorganisms occurring in nature but also produced by synthetic, chemical procedures. However, due to their poor efficacy or toxicity, most antifugal agents have not been utilized in commerce.

Antifungal agents in practical use do not function in a broad spectrum of activities nor do they exhibit a safe level of toxicity. These problems make it difficult to remedy deep antifungal infections. Moreover, since these antifungal agents do not have enough activities to kill fungi completely, rather having fungistatic activities, the use of those antifungal agents requires a long period of therapy. Therefore, there exists a need to develop novel antifungal agents having low toxicity, quick efficacy and fungicidal activity.

SUMMARY OF THE INVENTION

Cultivation of the novel microorganism *Pseudomonas cepacia* AF 2001 yields novel antibiotic substances Cepacidine A having powerful activities Against various yeasts and fungi, which have the formula:

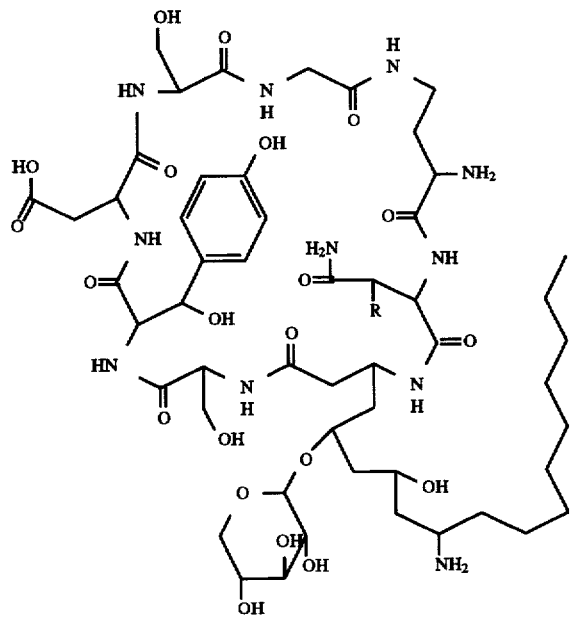

wherein R is H or OH. Where R is H, Cepacidine $A_2$ was designated; and where R is OH, Cepacidine $A_1$ was designated.

DESCRIPTION OF THE DRAWINGS

FIG. 1 shows the ultraviolet spectrum of Cepacidine A.

FIG. 2 shows the infrared spectrum of Cepacidine A in potassium bromide.

FIG. 3 shows the fast atom bombardment mass spectrum of Cepacidine A.

FIG. 4 shows the 400 MHz $^1$H NMR spectrum of Cepacidine A in deuterated dimethylsulfoxide.

FIG. 5 shows 100 MHz $^{13}$C NMR spectrum of Cepacidine A in deuterated dimethylsulfoxide.

FIG. 6 shows the pyrolyzed gas chromatograms of Cepacidine A, asparagine and aspartic acid.

DETAILED DESCRIPTION OF THE INVENTION

The Microorganism

*Pseudomonas cepacia* AF 2001 producing novel antifungal Cepacidine A was isolated from the soil samples collected in Munchon, Kyunggi-Do, Korea. The strain AF2001 was deposited at the Korean Federation of Culture Collections, Seoul, Korea, under the accession number KFCC 10773. The strain AF 2001 is a Gram-negative rod sized 0.4–0.6×1.0 –1.3 μm and motile by means of a polar flagella. It is oxidative and cytochrome positive. These characteristics serve to identify the strain as a Pseudemonas. A summary of the key characteristics and the carbon utilization pattern for the growth is shown in Table 1 below. The strain AF 2001 has similar characteristics to *Pseudemonas cepacia* disclosed in Bergy's manual of systematic bacteriology, 1984. However, the strain AF 2001 is different from *Pseudomonas cepacia* with regard to maltose, sucrose and adonitol utilization. It can grow on maltose and sucrose as a sole carbon source but can not grow on adonitol. In these aspects, the strain AF 2001 is thought to be a new *Pseudomonas cepacia*.

TABLE 1

Characteristics of *Pseudomonas cepacia* AF 2001

| | |
|---|---|
| Cell type | Short rod |
| Gram stain | Negative |
| Biochemical characteristics: | |
| Oxidative | Positive |
| Oxidase | Positive |
| Catalase | Positive |
| Urease | Negative |
| DNase | Negative |
| Lysine decarboxylase | Negative |
| Nitrate reduction | Negative |
| Poly β-hydroxybutyrate accumulation | Positive |
| Fluorescence | Negative |
| Diffusible pigment | Positive |
| Esculin hydrolysis | Positive |
| Benzene ring cleavage | Ortho |
| Growth at 4° C. | Negative |
| Growth at 41° C. | Positive |
| Growth at pH 3 | Negative |
| Growth at pH 9 | Positive |
| Carbon utilization: | |
| Positive: | maltose, sucrose, L-arabinose, mannose, xylose, fructose, tartarate, dulcitol, salicin, cellobiose, fumaric acid, caprate, threonine, lysine, arginine |
| Negative: | adonitol, D-raffinose, lactose, maleic acid, inulin, ethylene glycol, phthalic acid, L-isoleucine, starch, melibiose |

Production of the Antibiotic

Cultures of *Pseudomonas cepacia* AF 2001 were maintained at −85° C . When needed, working stock cultures were prepared on agar slants composed of glucose 3%, peptone 1.5% and agar 2%. The slants were incubated at 28°C. for 24 hours and used to inoculate germinator flasks containing 100 ml of medium in 500 ml Erlenmeyer flasks. This medium consisted of bactopeptone 1%, yeast extract 1% and glucose 3% The germinator was incubated for 24 hours at 28°C. on a rotary shaker at 300 rpm, and then used to inoculate(1%) the same medium(10 L). The fermentation was run for 72 hours at 28°C. with an agitation rate of 300 rpm. Progress of the fermentation and the subsequent isolation steps were monitored by paper-disc, agar diffusion assay with *Candida albicans* ATCC 38245 as the assay microorganism. Cepacidine A was isolated and purified by the procedure outlined in the diagram below. The fermentation broth(10 L) was mixed with an equal volume of isopropanol(10 L), and the mixture was adjusted to pH 4.0 with concentrated HCl. The mixture was centrifuged and the cell pellet was discarded. The supernatant was then concentrated under reduced pressure to remove isopropanol. The precipitate that formed during the concentration process contained the bioactivity, as shown by conventional agar diffusion assay. The concentrate and accompanying precipitate were stored at 4° C. for 6 hours to allow the precipitation to proceed to completion. The precipitate was collected by filtration with diatomaceous earth, washed with water and then eluted with 50% isopropanol in water. This solution was concentrated in vaccum to remove isopropanol. After extraction of this concentrate with isobutanol-methanol (8:2), the solvent extract was then concentrated under reduced pressure. The precipitate that formed during the concentration was collected by centrifugation and dissolved in 50% isopropanol adjusted to pH 10.0 with NaOH. This solution was diluted with 10 volume distilled water and applied to diaion HP-20 resin column chromatography. After elution with 50% isopropanol, the eluent was concentrated in vaccum to a small volume. The precipitate formed during the concentration was dissolved in 50% isopropanol and applied to alumina column chromatography. The passthrough that contained the bioactivity was concentrated to a small volume and stored at 4° C. for 24 hours to allow precipitation. After washing with water, the precipitate was dissolved in 50% isopropanol and applied on a preparative ODS-silica gel column of Waters μ-Bondapak C18 (3×30 cm, 10 μm) and developed with acetonitrile-water (6:4, pH 3.5). The fraction containing anti-candidal activity was collected and concentrated in vaccum to give residues of pure Cepacidine A (100 mg). Cepacidine A was further resolved into two closely related components, i.e., $A_1$ and $A_2$ by HPTLC on silica gel(Merck Silica gel 60 $F_{254}$), eluting with isopropanol-conc. ammonia-water(4:2:1). Visualization of the components was accomplished either by charring after spraying with a solution containing 5% ammonium molibdate and 0.1% ceric ammonium sulfate in 10% sulfuric acid or by spraying conventional ninhydrin reagent. The Rf values of $A_1$ and $A_2$ are 0.53 and 0.58, respectively. The producing ratio of $A_1$ and $A_2$ was determined to be 9:1 according to the quantitative analysis of the amounts of purified $A_1$ and $A_2$. Unfortunately, it was very difficult to isolate a large amount of pure $A_1$ and $A_2$, because Cepacidine A was not separated into $A_1$ and $A_2$ using the HPLC system described above. Therefore, the mixture of A and $A_2$ was used for the following studies, i.e., biological activity, physicochemical properties and structural elucidation.

Diagram on Isolation Procedures of Cepacidine $A_1$ and $A_2$

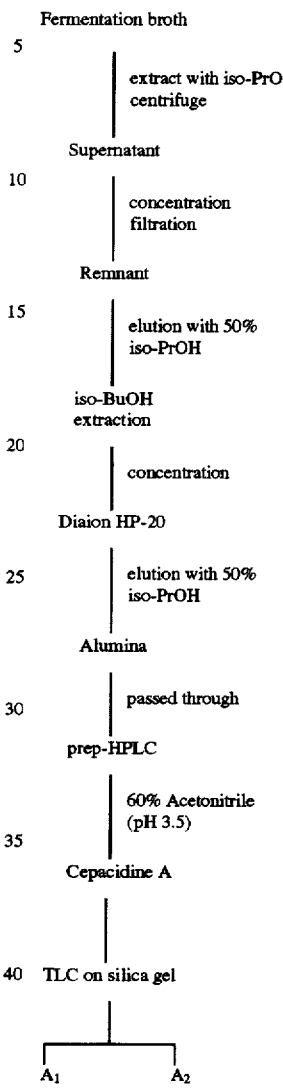

Biological Activity

The in vitro antifungal activities of Cepacidine A and amphotericin B against a broad range of medically important fungi are listed in Table 2. The activities were determined by the twofold agar dilution method on potato dextrose agar medium. Cepacidine A exhibited a broad antifungal spectrum against all strains tested. Particularly, Cepacidine A was highly active against dermatophytes, namely *Microsporum canis*, Trichophyton spp. and Epidermophyton spp., and true yeast at concentrations lower than 0.049 μml. The activities of Cepacidine A were greater than those of amphotericin B in most strains. However, no antibacterial activity was detected (MIC>100 μg/ml) when Cepacidine A was assayed against the bacteria i.e., *Bacillus subtilis*, *Escherichia coli*, *Staphylococcus aureus* and *Pseudomonas aeruginosa*.

TABLE 2

Antifungal spectrum of
Cepacidine A and Amphotericine-B

| | | MIC (μg/ml) | |
|---|---|---|---|
| organism | KCTC No* | Cepacidine A** | Amphotericin-B |
| Candida albicans | 1940 | 0.391 | 0.782 |
| Candida albicans | 38245 | 0.391 | 0.782 |
| Candida glabrata | 1714 | 0.013 | 0.196 |
| Cryptococcus neoformans | 1197 | 0.025 | 0.098 |
| Saccharomyces cerevisiae | 1213 | 0.049 | 0.098 |
| Aspergillus niger | 2119 | 0.098 | 0.196 |
| Microsporum gypseum | 1252 | 0.196 | 0.196 |
| Microsporum canis | 11621 | 0.025 | 0.391 |
| Epidennophyton floccosum | 1246 | 0.049 | 3.125 |
| Trichophyton mentagrophyte | 6085 | 0.049 | 3.125 |
| Trichophyton rubrum | 38484 | 0.049 | 0.782 |
| Fusarium oxysporum | 6084 | 0.196 | 0.196 |
| Rhizopus stolonifer | 6062 | 0.391 | 0.391 |

*:Korean Collection for Type Cultures
**:Two component mixture

Physico-chemical Properties

The physico-chemical properties of Cepacidine A are summarized in Table 3 below. Cepacidine A was isolated as white powder. The melting point ranged between 210° C. and 214° C. Cepacidine A is insoluble in ethyl acetate, hexane, ether and benzene, and is hardly soluble in water, methanol, ethanol, isopropanol, butanol and acetone, while it is soluble in DMSO, alkali aqueous solution and acidic aqueous solution. A 50% aqueous solution of alcohol increases solubility. Cepacidine A showed positive color reactions to aniline and ninhydrin reagents. The Rf value of Cepacidine A on silica gel TLC developed with n-butanol-acetic acid-water(3:1:1) was 0.18. However, the Rf values of Cepacidine A on silica gel TLC developed with isopropanol-water-saturated aqueous ammonia(4:1:2) were separated as 0.53 and 0.58 so that the compound with the Rf value of 0.53 was named Cepacidine $A_1$, and that with 0.58, Cepacidine $A_2$. Since Cepacidine $A_1$ and Cepacidine $A_2$ were hardly obtained separately by prep-HPLC, unfortunately, the mixture, Cepacidine A, was used for all spectrometric analyses, except TLC and amino acid analysis by HPLC. The mixture has a 9:1 ratio of Cepacidine $A_1$ and Cepacidine $A_2$. The UV spectrum of Cepacidine A dissolved in water showed two maximum absorption peaks at 232 nm and 274 nm, and the spectrum in DMSO showed only one peak at 278 nm. Cepacidine A is very stable in an aqueous solution between pH 2 and pH 11, while unstable in an aqueous solution above pH 11.5 so that Cepacidine A loses antifungal activities readily. The molecular formula of Cepacidine $A_1$ was determined to be $C_{52}H_{85}O_{22}N_{11}$ by HRFAB-MS, $^{13}C$ NMR and elemental analysis (calcd : C 51.4, H 7.0, N 12.7, O 29.0; found : C 51.5, H 8.0, N 11.0, O 29.5), Cepacidine $A_2$, $C_{52}H_{85}O_{21}N_{11}$. The molecular ions of Cepacidine $A_1$ and Cepacidine $A_2$ by HRFAB-MS were shown at m/z 1216.5999(MH$^+$, calcd: 1216.5949) and 1200.5978(MH$^+$, calcd.:1200.5999), respectively.

TABLE 3

Physico-Chemical Properties of Cepacidine A

| | Cepacidine $A_1$ | Cepacidine $A_2$ |
|---|---|---|
| appearance | white powders | white powders |
| MP | 210–214° C. | 210–214° C. |
| UV $\lambda_{max}$nm (log e) in $H_2O$ | 232 (2.8), 274 (1.7) | 232 (2.8), 274 (1.7) |
| in DMSO | 278 (1.2) | 278 (1.2) |
| IR (KBr) $\gamma_{max}$cm$^{-1}$ | 3352, 2924, 2854, 1666, 1539 | 3352, 2924, 2854, 1666, 1539 |
| | 1412, 1252, 1069, 557 | 1412, 1252, 1069, 557 |
| $[\alpha]_D^{25}$ $H_2O$ | +20.8 | +20.8 |
| TLC Rf value (n-BuOH: AcOH:$H_2O$ = 3:1:1) | 0.18 | 0.18 |
| (iso-PrOH:$H_2O$:said $NH_4OH$ = 4:1:2) | 0.53 | 0.58 |
| molecular formula | $C_{52}H_{85}O_{22}N_{11}$ | $C_{52}H_{85}O_{21}N_{11}$ |
| HRFAB-MS (M + H)$^+$ calcd | 1216.5949 | 1200.5999 |
| found | 1216.5999 | 1200.5978 |

Structure Elucidation

Since Cepacidine A showed positive color reaction to ninhydrin reagent, amino acid analysis was carried out by TLC and HPLC after acid hydrolysis. The analysis revealed Cepacidine $A_1$ consists of β-hydroxy Asx, Asx, Ser, Gly and 2,4-diaminobutyric acid(1:1:2:1:1), and Cepacidine $A_2$, Asx, Ser, Gly and 2,4-diaminobutyric acid(2:2:1:1). For amino acid analysis, the solution obtained from acid hydrolysis was eluted through octadecyl column. The remnant inside the column was washed with 50% isopropanol and collected for NMR experiments. The inspection of NMR experiments revealed the remnant is a type of β-amino acid with 18 carbons. This amino acid is a long chain of carbons with 3 functional groups and 1 methyl group, which were determined to be 1 primary amine and 2 hydroxyl groups by $^1H$ NMR, $^{13}C$ NMR, COSY, HETCOR, NOESY, HOHAHA and HMBC. Because Cepacidine A showed positive color reaction to aniline reagent, saccharide analysis was carried out by cellulose TLC and HPLC after acid hydrolysis. The analysis revealed both Cepacidine $A_1$ and Cepacidine $A_2$ include xylose.

The spectrum of Cepacidine A obtained from low resolution FAB-MS shows only MH$^+$ions of Cepacidine $A_1$ (m/z 1216) and Cepacidine $A_2$ (m/z 1200) except a few small fragments and xylose fragment. This phenomenon suggests Cepacidine A can be a cyclic peptide. The NMR experiments such as NOESY, HOHAHA and HMBC clarified this suggestion.

The sum of the calculated number of carbons of components obtained from amino acid analysis and saccharide analysis, and the number of carbons of C18 long chain amino acid is only 43. However, the $^{13}C$ NMR spectrum gives 50 peaks. Therefore, the presence of the other components can be considered. The $^1H$ NMR spectrum of Cepacidine A reveals the presence of aromatic ring. Since the four carbon signals at 114.70, 137.00, 132.20 and 156.50 ppm are characteristic peaks caused by para-hydroxy phenyl group, the presence of Tyr can be expected, but amino acid analysis with HPLC does not show the peak of Tyr so that the presence of a derivative of Tyr can be considered. In the COSY spectrum, cross peaks among 4.19, 5.06, 6.67 and 7.14 ppm are observed. In addition, HETCOR shows four correlated peaks such as 4.19/60.40, 5.06/70.96, 6.67/114.70 and 7.14/127.00($^1H$ NMR/$^{13}C$ NMR). These phenomena suggest one of β-protons of Tyr is substituted with a hydroxyl group. In order to clarify this, a chemical experiment was carried out. The UV spectrum of Cepacidine A in DMSO(FIG. 1) shows one peak at 278 nm. An addition of TFA into Cepacidine A caused bathochromic shift of λmax to 312 nm. An elimination of α-proton and β-proton of Tyr can cause a conjugation. Then, two carbon peaks at 114.70 and 127.00 in the $^{13}$C NMR spectrum must be ε and δ carbons of Tyr and denote two carbon intensity each. As a result, the number of carbon in Cepacidine A is not 50 shown in the $^{13}$C NMR spectrum but 52.

As mentioned before, molecular formula of Cepacidine A and Cepacidine $A_2$ was determined to be $C_{52}H_{85}O_{22}N_{11}$ and $C_{52}H_{85}O_{21}N_{11}$ by HRFAB-MS and elemental analysis. In order to determine Asx, pyrolyzed GC was carried out. Chromatograms of Asn and Asp as references are shown in FIG. 6. Two chromatograns can be distinguished by the characteristic peaks at retention time=47 min. Since the peaks of Cepacidine A at the same retention time are same as those of Asp, Asx contained in Cepacidine A must be Asp. NOESY and HOHAHA experiments have revealed xylose is connected to one of hydroxyl groups of C18 long chain amino acid. Here, if one counts all elements contained in the determined components of Cepacidine $A_1$, only β-hydroxy Asx is not counted. Until now Gly (1), Ser (2), Asp (1), β-hydroxy Tyr (1), 2,4-diaminobutyric acid (1), xylose (1), and C18 amino acid($C_{18}H_{38}O_4N_2$) were determined and the sum of elements contained in those components are $C_{48}H_{95}O_{27}N_9$. However, because Cepacidine A is a cyclic peptide and xylose is connected to C18 amino acid, the formula must be $C_{48}H_{79}O_{19}N_9$. The difference between this formula and that obtained from HRFAB-MS gives $C_4H_6O_3N_2$ for Cepacidine $A_1$. Therefore, the undetermined components, β-hydroxy Asx of Cepacidine $A_1$ must be β-hydroxy Asn, and Asx of Cepacidine $A_2$, Asn, respectively. The components of Cepacidine $A_1$ and Cepacidine $A_2$ are listed in Table 4.

TABLE 4

Components of Cepacidine $A_1$ and $A_2$

| components | Cepacidine $A_1$ | Cepacidine $A_2$ |
|---|---|---|
| Glycine | 1 | 2 |
| Serine | 2 | 2 |
| Aspartic acid | 1 | 1 |
| Asparagine | 0 | 1 |
| β-Hydroxyasparagine | 1 | 1 |
| 2,4-Diaminobutyric acid | 1 | 1 |
| β-Hydroxytyrosine | 1 | 1 |
| $C_{18}$Amino acid | 1 | 1 |
| Xylose | 1 | 1 |

Experimental

FAB-MS was measured on a Jeol DX 303 spectrometer. UV and IR were recorded on a Beckman DU-70, and on a Bruker IFS 66, respectively. NMR spectra were recorded on a Bruker ARX 400 spectrometer in DMSO-$d_6$ and 95% DMSO-$d_6$/5% $D_2O$. The elemental analysis data were obtained on Foss Heraeus CHN-0-Rapid. TLC was performed on pre-coated Silica gel plates(Merck catalog No. 5642). Pyrolysed GC was measured on a Schimadzu GC 15A and a JHP-35 Pyrolyser with a CBP-5 column. For amino acid analysis Cepacidine A was hydrolyzed with 6N HCl at 105° C. for 8 hr. and Waters amino acid conversion kit and Waters amino acid analysis column were used, Waters Fluorescence 420, as a detector. For saccharide analysis, Cepacidine A was hydrolyzed with 10% $H_2SO_4$ at 100°C. for 1 hr, and Waters carbohydrate analysis system and Waters carbohydrate column were used, Waters R1410, as a detector.

What is claimed is:

1. An antifungal compound having the following formula:

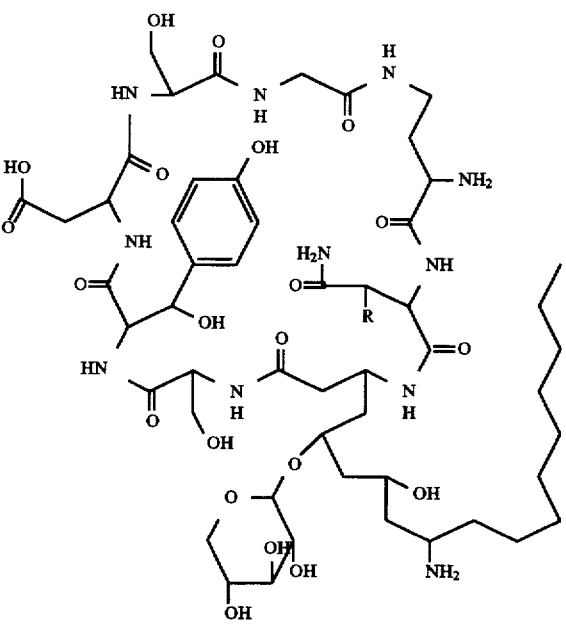

wherein R is H or OH.

2. An isolated microorganism Pseudomonas sp. AF 2001.

3. A process for producing the antifungal antibiotics according to claim 1, which process comprises fermentation of a microorganism Pseudomonas sp. AF 2001, and extracting and purfying the fermentation broth of said strain to obtain said antibiotics.

* * * * *